United States Statutory Invention Registration [19]

[11] Reg. Number: H78

Adolph et al. [45] Published: Jul. 1, 1986

[54] 5-AZA-3,3,7,7-TETRANITRONONANE-1,9-DIOLS AND METHOD OF PREPARATION

[75] Inventors: Horst G. Adolph, Silver Spring; Michael E. Sitzmann, Adelphi, both of Md.

[73] Assignee: The United States of America as represented by the Secretary of the Navy, Washington, D.C.

[21] Appl. No.: 492,276

[22] Filed: May 6, 1983

[51] Int. Cl.[4] ..... C07C 69/76

[52] U.S. Cl. ..... 560/110; 560/264; 560/8; 560/30; 564/111; 564/113; 564/506; 564/106; 562/512; 149/92

[58] Field of Search ..... 149/92; 560/110, 264, 560/8, 30; 260/465.5 R; 562/512; 564/111, 113, 506; 568/231

[56] References Cited

U.S. PATENT DOCUMENTS

| | | | |
|---|---|---|---|
| 2,731,460 | 1/1956 | Schenck et al. | 564/111 |
| 3,000,933 | 9/1961 | Herzog | 560/264 |
| 3,000,957 | 9/1961 | Gold et al. | 564/111 |
| 3,000,958 | 9/1961 | Gold et al. | 564/111 |
| 3,040,099 | 6/1962 | Feuer et al. | 564/111 |
| 3,066,169 | 11/1962 | Feuer et al. | 564/111 X |
| 3,396,187 | 8/1968 | Benzinger | 560/264 X |
| 3,474,092 | 10/1969 | Dinwoodie et al. | 560/251 X |
| 3,590,067 | 6/1971 | Gold | 560/264 |
| 4,128,583 | 12/1978 | Wiener et al. | 564/111 |

FOREIGN PATENT DOCUMENTS

| | | | |
|---|---|---|---|
| 650551 | 10/1962 | Canada | 568/712 |
| 268402 | 4/1970 | U.S.S.R. | 564/111 |

OTHER PUBLICATIONS

Fridman, et al. "Formation of gamma . . . " Zhur. Org. Khim. 10(10) p. 2053–6, 1975.

Mukhametshin, et al. "Behavior of Nitrated Nitroso . . ." Zhur. Org. Khim. 6(5) 928–929, 1970.

Mukhametshin, et al. "Cyclization of Nitro . . . " 4(5) 920, 1968.

*Primary Examiner*—John F. Terapane
*Assistant Examiner*—Susan Wolffe
*Attorney, Agent, or Firm*—Kenneth E. Walden; Roger D. Johnson

[57] ABSTRACT

Energetic diols of the formula $$HOCH_2CH_2C(NO_2)_2CH_2\overset{\overset{\displaystyle R}{|}}{N}CH_2C(NO_2)_2CH_2CH_2OH$$

wherein R is —H, —NO, —$NO_2$, —CN, or —$CH_2COOH$, and diesters of the formula $$R'\overset{\overset{\displaystyle O}{\|}}{C}OCH_2CH_2C(NO_2)_2CH_2\overset{\overset{\displaystyle R}{|}}{N}CH_2C(NO_2)_2CH_2CH_2O\overset{\overset{\displaystyle O}{\|}}{C}R'$$

wherein R is —H, —NO, —$NO_2$, —CN, —$CH_2COOCH_3$, —$CH_2COOCH_2C(NO_2)_2CH_3$, or —$CH_2COOCH_2C(NO_2)_3$ and R′ is an alkyl, fluoroalkyl, chloroalkyl, aryl, fluoroaryl, chloroalkyl, aralkyl, fluoroaralkyl, chloroaralkyl, or alkene group.

22 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

5-AZA-3,3,7,7-TETRANITRONONANE-1,9-DIOLS AND METHOD OF PREPARATION

BACKGROUND OF THE INVENTION

This invention relates to alcohols and more particularly to energetic polynitro substituted diols.

Previously, polynitrodiols such as A-Diol and DINOL were used as components of energetic polymers. These diols are known to fragment easily with loss of formaldehyde and formation of labile dinitromethane derivatives. Thus when free hydroxy groups are present in the polymer they provide sites for initiation of thermal decomposition and chemical reactions (incompatibility with other ingredients, degradation during aging). In particular, it would be desirable to provide diols which will be more stable toward weak bases or nucleophiles such as water (atmospheric moisture) or oxygen and nitrogen containing components of energetic binder systems.

SUMMARY OF THE INVENTION

Accordingly, an object of this invention is to provide new energetic diols.

Another object of this invention is to provide new energetic diols which can be used as components in energetic propellant and explosive binders.

A further object of this invention is to provide new polynitro diols which resist deformylation by mild bases.

Yet another object of this invention is to provide new polynitro diols which are compatible with oxygen and nitrogen containing components of propellant and explosive composites.

These and other objects of this invention are accomplished by providing diols of the formula $$HOCH_2CH_2C(NO_2)_2CH_2\overset{\overset{\displaystyle R}{|}}{N}CH_2C(NO_2)_2CH_2CH_2OH$$

wherein R is —H, —NO, —$NO_2$, —CN, —$CH_2COOCH_3$, —$CH_2COOCH_2C(NO_2)_2CH_3$, or —$CH_2COOCH_2C(NO_2)_3$.

DETAILED DESCRIPTION OF THE PREFERRED EMBODIMENT

The compounds of the present invention are energetic diols of the formula $$HOCH_2CH_2C(NO)_2CH_2\overset{\overset{\displaystyle R}{|}}{N}CH_2C(NO_2)_2CH_2CH_2OH$$

and their corresponding diesters of the formula $$R'\overset{\overset{\displaystyle O}{\|}}{C}OCH_2CH_2C(NO_2)_2CH_2\overset{\overset{\displaystyle R}{|}}{N}CH_2C(NO_2)_2CH_2CH_2O\overset{\overset{\displaystyle O}{\|}}{C}R'$$

wherein R is —H, —NO, —$NO_2$, —CN, —$COOCH_3$, —$COOCH_2C(NO_2)_2CH_3$, or —$COOCH_2C(NO_2)_3$ and R′ is an alkyl, fluoroalkyl, chloroalkyl, aryl, fluoroaryl, chloroalkyl, aralkyl, fluoroaralkyl, chloroaralkyl, or alkene group.

The critical feature of the diols of the present invention is that the gem-dinitro groups are located in the $\gamma$ position to the hydroxy groups $$-C(NO_2)_2CH_2CH_2OH.$$

In similar prior art diols the gem-dinitro groups are located in the $\beta$ position adjacent to the hydroxy groups $$-C(NO_2)_2CH_2OH.$$

As stated in the background of the invention, these prior art diols are known to fragment easily in the presence of oxygen or nitrogen containing components of energetic binder systems. As a result, loss of formaldehyde and formation of labile dinitromethane derivatives occurs. Polymers made with these $\beta$-dinitro diols are therefor less stable. In the present diols, the additional methylene group between the gem-dinitro and the hydroxy group prevents the deformylation reaction. Therefore, binder polymers made with these new diols will be much more stable than those of the prior art. The addition of still more methylene groups is not desirable as they will lower the energy content of the present diols without significantly improving their stability.

5-aza-3,3-7,7-tetranitrononane-1,9-diol can be prepared by reacting one mole of ammonia with two moles of 2,2-dinitrobutane-1,4-diol under the conditions given in example 7.

$$2HOCH_2CH_2C(NO_2)_2CH_2OH + NH_3 \longrightarrow HOCH_2CH_2C(NO_2)_2CH_2\overset{\overset{\displaystyle H}{|}}{N}CH_2C(NO_2)_2CH_2CH_2OH.$$

A method of preparing 2,2-dinitrobutane-1,4-diol is disclosed in U.S. Pat. Ser. No. 492,277, filed on May 6, 1983, entitled "2,2-Dinitrobutane-1,4-diol and Monoesters," by Horst G. Adolph and Michael Sitzmann, which was filed concurrently with the present case, herein incorporated by reference. In the process, 3,3,3-trinitropropanol is reacted with potassium iodide to produce the salt potassium 3,3-dinitropropanol.

$$C(NO_2)_3CH_2CH_2OH + KI \rightarrow K^+{}^-C(NO_2)_2CH_2CH_2OH.$$

The salt is then reacted with formaldehyde and the solution is acidified to yield the 2,2-dinitrobutane-1,4-diol $$K^+{}^-C(NO_2)_2CH_2CH_2OH + CH_2O \xrightarrow{H^+} HOCH_2C(NO_2)_2CH_2CH_2OH.$$

5-aza-3,3,7,7-tetranitrononane-1,9-diol-1,9-diesters of the formula $$R'\overset{\overset{\displaystyle O}{\|}}{C}OCH_2CH_2(NO_2)_2CH_2\overset{\overset{\displaystyle H}{|}}{N}CH_2C(NO_2)_2CH_2CH_2O\overset{\overset{\displaystyle O}{\|}}{C}R'$$

can be formed by reacting one mole of ammonia with two moles of a monoester of the formula $$HOCH_2C(NO_2)_2CH_2CH_2O\overset{\overset{\displaystyle O}{\|}}{C}R'.$$

The monoester may be prepared according to the procedure disclosed in U.S. Patent Application Ser. No. 492,277, filed on May 6, 1983, entitled "2,2-DINITROBUTANE-1,4-DIOL AND MONOESTERS," supra, which was filed concurrently with the present application, and herein incorporated by reference. First, 3,3,3-trinitropropanol is esterified by conventional means to produce a compound of the formula $$C(NO_2)_3CH_2CH_2O\overset{O}{\overset{\|}{C}}R'.$$

For example, the alcohol may be reacted with the appropriate acid chloride $$C(NO_2)_3CH_2CH_2OH + R'\overset{O}{\overset{\|}{C}}Cl \longrightarrow C(NO_2)_3CH_2CH_2O\overset{O}{\overset{\|}{C}}R'.$$

Example 2 illustrates this step for R′ equal to —$CH_3$ $$C(NO_2)_3CH_2CH_2OH + CH_3\overset{O}{\overset{\|}{C}}-Cl \longrightarrow C(NO_2)_3CH_2CH_2O\overset{O}{\overset{\|}{C}}CH_3.$$

Next, the ester is reacted with potassium iodide to produce a potassium salt $$C(NO_2)_3CH_2CH_2O\overset{O}{\overset{\|}{C}}R' + KI \longrightarrow K^{+-}C(NO_2)_2CH_2CH_2O\overset{O}{\overset{\|}{C}}R'.$$

Example 3 illustrates this step for R′ equal to —$CH_3$ $$C(NO_2)_3CH_2CH_2O\overset{O}{\overset{\|}{C}}CH_3 + KI \longrightarrow K^{+-}C(NO_2)_2CH_2CH_2O\overset{O}{\overset{\|}{C}}CH_3.$$

Reaction of the potassium salt of the ester, formaldehyde, and ammonia yields the desired diester $$2K^{+-}C(NO_2)_2CH_2CH_2O\overset{O}{\overset{\|}{C}}R' + 2CH_2O + NH_3 \xrightarrow{H^+} R'\overset{O}{\overset{\|}{C}}OCH_2CH_2C(NO_2)_2CH_2\overset{H}{\overset{|}{N}}CH_2C(NO_2)_2CH_2CH_2O\overset{O}{\overset{\|}{C}}R'.$$

Example 4 illustrates this step for R equal to —$CH_3$ $$2K^{+-}C(NO_2)_2CH_2CH_2O\overset{O}{\overset{\|}{C}}CH_3 + 2CH_2O + NH_3 \xrightarrow{H^+} CH_3\overset{O}{\overset{\|}{C}}OCH_2CH_2C(NO_2)_2CH_2\overset{H}{\overset{|}{N}}CH_2C(NO_2)_2CH_2CH_2O\overset{O}{\overset{\|}{C}}CH_3.$$

The ester groups can be hydrolyzed off by conventional means (for instance see Example 6). Because the $$R\overset{O}{\overset{\|}{C}}-$$

serves only as a blocking group and is later hydrolyzed off, selection of R is not critical. For example, R may be an alkyl, fluoroakyl, chloroalkyl, aryl, fluoroaryl, chloroalkyl, aralkyl, fluoroaralkyl, chloroaralkyl, or alkene group. The only restrictions are that R should contain no groups that will interfer with the esterification of the 3,3,3-trinitropropanol or with the reaction between the 2,2-dinitrobutane-1,4-diol monoester and ammonia. (Amino and hydroxy containing groups are therefore not included in R.) As a practical matter, R is preferably low in molecular weight. For example, when R is an alkyl, fluoroalkyl, or chloroalkyl group, R preferable contains from 1 to 12, and more preferably from 1 to 4 carbon atoms. When R is an aryl, fluoroaryl, or chloroaryl groups, R preferably contains from 6 to 18, and more preferably 6 carbon atoms. When R is an aralkyl, fluoroalkyl, or chloroaralkyl group, R preferably contains from 7 to 18, and more preferably from 7 to 10 carbon atoms. Of all the groups available, R equals to —$CH_3$ is most preferred for industrial purposes because of cost.

Other common examples are R equal to —CH=$CH_2$,

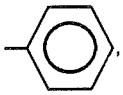

—$CF_3$, —$CCl_3$, etc.

The 3,3,7,7-tetranitro-5-azanonane-1,9-diol and its 1,9-diester derivatives are secondary amines with an active N-hydrogen which can be replaced with a more energetic group. For instance, Example 5 illustrate the nitration of the diacetate to form 3,3,5,7,7-pentanitro-5-azanonane-1,9-diol-1,9-diacetate using 90% nitric acid and acetic anhydride, $$[CH_3\overset{O}{\overset{\|}{C}}OCH_2CH_2C(NO_2)_2CH_2]_2NH \xrightarrow[\text{acetic anhydride}]{90\%\ HNO_3} [CH_3\overset{O}{\overset{\|}{C}}OCH_2CH_2C(NO_2)_2CH_2]_2N-NO_2.$$

Example 6 shows the acid hydrolysis of this diacetate to form 3,3,5,7,7-pentanitro-5-azanonane-1,9-diol, $$[CH_3\overset{O}{\overset{\|}{C}}OCH_2CH_2C(NO_2)_2CH_2]_2N-NO_2 \xrightarrow{H^+,\ H_2O} [HOCH_2CH_2C(NO_2)_2CH_2]_2N-NO_2.$$

Acetic acid and sodium nitrite, $NaNO_2$, have been used under standard conditions to nitrosate 3,3,7,7-tetranitro-5-azanone-1,9-diol-1,9-diacetate to form 3,3,7,7-tetranitro-5-nitroso-5-azanonane-1,9-diol-1,9-diacetate $$[CH_3\overset{O}{\overset{\|}{C}}OCH_2CH_2C(NO_2)_2CH_2]_2NH \xrightarrow[\text{acetic acid}]{NaNO_2} [CH_3\overset{O}{\overset{\|}{C}}OCH_2CH_2C(NO_2)_2CH_2]_2N-NO.$$

Similarly, acetic acid and sodium nitrite may be used under standard conditions to nitrosate 3,3,7,7-tetranitro-5-azanone-1,9-diol to form 3,3,7,7-tetranitro-5-nitroso-5-azanone-1,9-diol.

$$[HOCH_2CH_2C(NO_2)_2CH_2]_2NH \xrightarrow[\text{acetic acid}]{NaNO_2} [HOCH_2CH_2C(NO_2)_2CH_2]_2N{-}NO.$$

3,3,7,7-tetranitro-5-cyano-5-azanonane-1,9-diol $$[HOCH_2CH_2C(NO_2)_2CH_2]_2NCN$$

and its diester derivatives (e.g., 3,3,7,7-tetranitro-5-cyano-5-azanonane-1,9-diol 1,9-diacetate where $R'=CH_3$)

$$[R'\overset{O}{\overset{\|}{C}}OCH_2CH_2C(NO_2)_2CH_2]_2NCN$$

can be prepared by reaction of the corresponding secondary amines with cyanogen bromide.

By reacting 2 moles of a 4-monoester of 2,2-dinitrobutane-1,4-diol with glycine $$2R'\overset{O}{\overset{\|}{C}}OCH_2CH_2C(NO_2)_2CH_2OH + H_2NCH_2COOH \longrightarrow [R'\overset{O}{\overset{\|}{C}}OCH_2CH_2C(NO_2)_2CH_2]_2NCH_2COOH$$

the 1,9 diester can be produced. The carboxylic acid group on the N,N-disubstituted glycine product could then be esterified with the appropriate alcohol by standard methods. For instance if methanol is used the product ester would be $[HOCH_2CH_2C(NO_2)_2CH_2]_2NCH_2COOCH_3$. If 2,2-nitropropanol is used the product ester would be $[HOCH_2CH_2C(NO_2)_2CH_2]_2NCH_2COOCH_2C(NO_2)_2CH_3$. Finally, if 2,2,2-trinitroethanol is used, the product ester will be $[HOCH_2CH_2C(NO_2)_2CH_2]_2NCH_2COOCH_2C(NO_3)_3$. Alternately, the 1,9-ester groups could be hydrolyzed off by conventional means to yield the diol $$[R'\overset{O}{\overset{\|}{C}}OCH_2CH_2C(NO_2)_2CH_2]_2NCH_2COOH \xrightarrow{H^+,\ H_2O} [HOCH_2CH_2C(NO_2)_2CH_2]_2NCH_2COOH.$$

The feasibility of these glycine syntheses is illustrated by similar syntheses in "The Mannich Reaction of 2,2-Dinitro-1-alkanols with Ammonia, Glycine and Hydrazine," by Milton B. Frankel and Karl Klager, Journal of the American Chemical Society, Vol. 79, pp. 2953-6 (1957), herein incorporated by reference. In particular the following 2 Examples are quoted from that article p. 2954, col. 2:

Bis-(2,2-dinitropropyl)-glycine (IV). A solution of 7.5 g. (0.1 mole) of glycine, 4.0 g. (0.1 mole) of sodium hydroxide and 50 ml. of water was mixed with 15.0 g. (0.1 mole) of 2,2-dinitropropanol. The temperature rose to 42° and the yellow solution formed was allowed to stand overnight. Upon addition of dilute sulfuric acid a viscous, colorless oil separated and solidified on standing. The product 15.6 g. (92.0%) was collected and recrystallized from methanol-water to give white crystals, m.p. 123°–124°.

Methyl Bis-(2,2-dinitropropyl)-glycine. A mixture of 20 g. (0.059 mole) of bis-(2,2-dinitropropyl)-glycine, 100 ml. of methanol and 10.0 ml. of concentrated sulfuric acid was refluxed for 90 minutes. The solution was diluted with 250 ml. of methylene chloride and washed with water, 5% sodium carbonate solution and water. The solvent was evaporated to yield 14.0 g. (67.3%) of white solid. Recrystallization from methanol-ether gave crystals, m.p. 94°–95°.

The general nature of this invention having been set forth, the following examples are set forth as specific illustrations thereof. It will be understood that the invention is not limited to these specific examples but is susceptible to various modifications that will be recognized by one of ordinary skill in the art.

Example 1

Preparation of 3,3,3-trinitropropanol 4,4,4-Trinitrobutyric acid (210 g, 0.94 mol) was added to 534 ml (908 g) of trifluoromethanesulfonic acid stirred in a 2000 ml, 3-neck, round-bottom flask. The solution was heated to 60° C. (oil bath) and sodium azide (100 g, 1.54 mol) was added in approximately 2 g portions over a six-hour period. (A stream of nitrogen was kept flowing over the reaction mixture during the addition to dilute and expel excess $HN_3$.) Stirring was stopped and the thick mixture was heated overnight at 50° C. before it was poured onto ice to give an aqueous solution (2500 ml) which was extracted with 3×300 ml of methylene chloride. Two grams of unreacted trinitrobutyric acid were recovered from the $CH_2Cl_2$ extracts. The aqueous solution was cooled at 10°–14° C. while a solution of 140 g of sodium hydroxide in 200 ml of water was added dropwise with good stirring. The solution was then heated to 35° C. before a solution of 121 g (1.75 mol) of sodium nitrite in 400 ml of water was added over a 30 minute period. (Some cooling was necessary to maintain the temperature at approximately 40° C. during the addition.) The solution was heated at 60° C. for one and a half hours before it was cooled to 25° C. and extracted with 2×500 ml methylene chloride. It was then saturated with sodium chloride and extracted with 3×500 ml $CH_2Cl_2$. The combined extracts contained 161 g (87.7 percent) of crude 3,3,3-trinitropropanol.

EXAMPLE 2

Preparation of 3,3,3-Trinitropropyl Acetate

Acetyl chloride (125 ml) was added to a dried ($MgSO_4$) solution of 150 g of crude 3,3,3-trinitropropanol as prepared above and cooled in an icebath. The solution was slowly warmed to reflux temperature and held overnight. The reaction solution was concentrated to 800 ml by distillation before it was cooled and poured onto ice water. The mixture was stirred for 30 minutes before the $CH_2Cl_2$ layer was separated, dried over $MgSO_4$, and the solvent removed to give 183 g (100 percent) of crude 3,3,3-trinitropropyl acetate as a light green solid. A similar reaction employing 31.9 g of crude 3,3,3-trinitropropanol, 50 ml of methylene chloride and 25 ml of acetyl chloride gave, after addition of hexane to the $CH_2Cl_2$ solution and chilling, filtering off the solid, concentrating and chilling again, 34.5 g (88.9 percent) of 3,3,3-trinitropropyl acetate. A second recrystallization from $CH_2Cl_2$/hexane gave material of mp 47°–49° C.; $^1H$ NMR ($CDCl_3$); δ2.06 (s, 3H), 3.45 (t, 2H), 4.55 (t, 2H).

Analysis:

Calculated for $C_5H_7N_3O_8$: C, 25.32; H, 2.98; N, 17.72. Found: C, 25.31; H, 3.01; N, 17.27.

EXAMPLE 3

Preparation of Potassium 3,3-Dinitropropyl Acetate

Potassium iodide (338 g, 2.03 mol) was added to 183 g (0.77 mol) of crude 3,3,3-trinitropropyl acetate in 2100 ml of methanol. The mixture was stirred at 40° C. for 24 hours before it was cooled to 20° C. and the yellow salt removed by filtration. The product was stirred with 600 ml of methanol at 20° C. to give 88.5 g (50 percent) of yellow salt.

A similar reaction using 32.1 g of purified 3,3,3-trinitropropyl acetate gave 20.4 g (66 percent) of potassium 3,3-dinitropropyl acetate. $^1H$ NMR ($D_2O$ with TMS capillary): δ2.54 (s, 3H), 3.94 (t, 2H), 4.93 (t, 2H).

EXAMPLE 4

Preparation of 3,3,7,7-Tetranitro-5-azanonane-1,9-diol-1,9-diacetate

A solution of potassium 3,3-dinitropropyl acetate (87 g, 0.38 mol) in 1050 ml of distilled water and 84 ml of 36 percent formalin was stirred in an ice bath while 45 ml of concentrated hydrochloric acid was added (pH approximately 3). The mixture was heated at 40° C. for 30 minutes, then cooled to 20° C. and 42.6 g of ammonium chloride was added. The mixture was stirred vigorously in an ice bath while concentrated ammonium hydroxide solution was added over several hours until the aqueous phase remained yellow and the pH was 5.5 to 6. At this point an appreciable amount of semisolid had separated from solution and adhered to the walls of the flask. The mixture was stirred overnight before the semisolid was extracted into methylene chloride. Addition of hexane and cooling to 5° C. gave 58.1 g of white crystals, mp 75°–76° C. The mother liquor was cooled in dry ice-acetone to give a semisolid which was stirred with water and then crystallized from methylene chloride-hexane to give an additional 3.0 g of product, mp 66°–70° C. Total yield (61.1 g) is 76 percent of theoretical. The analytical sample had mp 75.5°–76° C. $^1H$ NMR ($CDCl_3$): δ2.06 (s, 3H), 2.91 (t, 2H), 3.85 (d, 2H), 4.27 (t, 2H).

Analysis:

Calculated for $C_8H_{14}N_6O_{12}$: C, 33.89; H, 4.50; N, 16.47. Found: C, 33.93; H, 4.62; N, 16.19.

EXAMPLE 5

Preparation of 3,3,5,7,7-Pentanitro-5-azanonane-1,9-diol-1,9-diacetate

Acetic anhydride (315 ml) was stirred in an ice bath to maintain a temperature of 20°–23° C. during the slow addition of 95 ml of 90 percent nitric acid. The solution was then cooled to 5° C. while 3,3,7,7-tetranitro-5-azanonane-1,9-diol-1,9-diacetate was added in portions with good stirring. The solution was stirred at ambient temperature overnight before it was poured into ice water. The mixture was stirred for one hour and the solid (66.5 g, 97 percent, mp 87°–89° C.) was removed by filtration. A recrystallized sample ($CH_2Cl_2$/hexane) had mp 88°–89° C.; $^1H$ NMR ($CDCl_3$): δ2.09 (s, 3H), 3.00 (t, 2H), 4.35 (t, 2H), 5.20 (s, 2H).

EXAMPLE 6

Preparation of 3,3,5,7,7-Pentanitro-5-azanonane-1,9-diol

Crude 3,3,5,7,7-pentanitro-5-azanonane-1,9-diol-1,9-diacetate (66.5 g) was stirred in 615 ml of warm (50° C.) MeOH in a 2000 ml round-bottom flask. Distilled water (265 ml) was added followed by 19 ml of concentrated hydrochloric acid. The mixture was heated at 67°–69° C. (mild reflux) overnight before nearly all the solvent was removed under reduced pressure on a rotary evaporator (water bath at 35° C.). The white solid (mp 118°–120° C.) was removed by filtration and washed with cold water. Crystallization from methanol-water gave 50.0 g, mp 121.5°–123° C. The second crop (2.9 g, mp 118°–120° C.) raised the yield to 52.9 g (97 percent). $^1H$ NMR (acetone-$d_6$+1 dr. $D_2O$): δ3.00 (t, 2H), 2.90 (t, 2H), 5.57 (s, 2H).

Analysis:

Calculated for $C_8H_{14}N_6O_{12}$: C, 24.88; H, 3.65; N, 21.76. Found: C, 24.97; H, 3.70; N, 21.66.

EXAMPLE 7

Preparation of 5-aza-3,3,7,7-tetranitrononane-1,9-diol

Thirty percent aqueous ammonium hydroxide (0.60 g, 0.0105 mol) was diluted to 5 ml with distilled water before it was slowly added over a 1.5 hour period to a solution of 1.80 g 0.01 mol) of 2,2-dinitrobutane-1,4-diol and 1.20 g (0.022 mol) of ammonium chloride in 25 ml of distilled water stirred at ambient temperature. The aqueous solution was decanted from a sticky semisolid percipitate which was washed with water and then dissolved in ether. A very small amount of ether insoluble solid was removed before the ether was evaporated to give 0.28 g of solid, mp 67°–72° C. Crystallization from methylene chloride raised the melting point to 76°–78° C. $^1H$ NMR ($CD_2Cl_2$): δ3.95 (d, 4H), 3.88 (t, 4H), 2.86 (t, 4H), 2.36 (m, 1H), 1.91 (s, 2H); IR (KBr) 3600–3100 (OH), 3380 (NH), 1590, 1570 ($NO_2$) $cm^{-1}$.

Analysis:

Calculated for $C_8H_{15}N_{15}O_{10}$: C, 28.16; H, 4.43; N, 20.52. Found: C, 28.28; H, 4.40; N, 20.34.

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A compound of the formula $$HOCH_2CH_2C(NO_2)_2CH_2\overset{\overset{\displaystyle R}{|}}{N}CH_2C(NO_2)_2CH_2CH_2OH$$

wherein R is selected from the group consisting of —H, —NO, —$NO_2$, —CN, and —$CH_2COOH$.

2. The compound of claim 1 wherein R is H.

3. The compound of claim 1 wherein R is —NO.

4. The compound of claim 1 wherein R is —$NO_2$.

5. The compound of claim 1 wherein R is —CN.

6. The compound of claim 1 wherein R is —$CH_2COOH$.

7. A compound of the formula $$R'\overset{O}{\overset{\|}{C}}OCH_2CH_2C(NO_2)_2CH_2\overset{R}{\overset{|}{N}}CH_2C(NO_2)_2CH_2CH_2O\overset{O}{\overset{\|}{C}}R'$$

wherein R is selected from the group consisting of —H, —NO, —$NO_2$, —CN, —$CH_2COOCH_3$, —$CH_2COOCH_2C(NO_2)_2CH_3$, and —$CH_2COOCH_2C(NO_2)_3$ and R′ is selected from the group consisting of alkyls, fluoroalkyls, chloroalkyls, aryls, fluoroaryls, chloroaryls, aralkyls, fluoroaralkyls, chloroaralkyls, and alkenes.

8. The compound of claim 7 wherein R is —H.

9. The compound of claim 7 wherein R is —NO.

10. The compound of claim 7 wherein R is —$NO_2$.

11. The compound of claim 7 wherein R is —CN.

12. The compound of claim 7 wherein R is —$CH_2COOCH_3$.

13. The compound of claim 7 wherein R is —$CH_2COOCH_2C(NO_2)_2CH_3$.

14. The compound of claim 7 wherein R is —$CH_2COOCH_2C(NO_2)_3$.

15. The compound of claim 7 wherein R is —$CH_2COOH$.

16. The compound of claim 7 wherein R′ is selected from the group consisting of alkyls, fluoroalkyls, and chloroalkyls having from 1 to 12 carbon atoms.

17. The compound of claim 16 wherein R′ contains from 1 to 4 carbon atoms.

18. The compound of claim 7 wherein R′ is selected from the group consisting of aryls, fluoroaryls, and chloroaryls having from 6 to 18 carbon atoms.

19. The compound of claim 18 wherein R′ has 6 carbon atoms.

20. The compound of claim 7 wherein R′ is selected from the group consisting of aralkyls, fluoroaralkyls, and chloroaralkyls of from 7 to 18 carbon atoms.

21. The compound of claim 20 wherein R′ contains from 7 to 10 carbon atoms.

22. The compound of claim 7 wherein R′ is vinyl.

* * * * *